United States Patent
Shida

(10) Patent No.: US 9,516,235 B2
(45) Date of Patent: Dec. 6, 2016

(54) FLUORESCENCE OBSERVATION APPARATUS AND FLUORESCENCE OBSERVATION METHOD

(71) Applicant: OLYMPUS CORPORATION, Tokyo (JP)

(72) Inventor: Hiromi Shida, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 389 days.

(21) Appl. No.: 14/091,673

(22) Filed: Nov. 27, 2013

(65) Prior Publication Data

US 2014/0078279 A1   Mar. 20, 2014

Related U.S. Application Data

(63) Continuation of application No. PCT/JP2012/064085, filed on May 31, 2012.

(30) Foreign Application Priority Data

Jun. 3, 2011   (JP) ................................. 2011-125524

(51) Int. Cl.
  *H04N 5/235* (2006.01)
  *G06T 7/00* (2006.01)
  (Continued)

(52) U.S. Cl.
  CPC ............. *H04N 5/235* (2013.01); *A61B 1/0005* (2013.01); *A61B 1/00009* (2013.01); (Continued)

(58) Field of Classification Search
  CPC ... A61B 1/00009; A61B 1/0005; A61B 1/043; G01N 21/6456; G06T 2207/10064; G06T 2207/10068; G06T 2207/30004; G06T 2207/30241; G06T 7/0083; G06T 7/0097; G06T 7/2033; H04N 5/235
  (Continued)

(56) References Cited

U.S. PATENT DOCUMENTS

| | | | | |
|---|---|---|---|---|
| 8,655,043 | B2* | 2/2014 | Dixon ................ | G01N 21/6428 382/128 |
| 2001/0053247 | A1* | 12/2001 | Sowinski ........... | H04N 1/00132 382/162 |

(Continued)

FOREIGN PATENT DOCUMENTS

| JP | 2010-017396 A | 1/2010 |
|---|---|---|
| JP | 4587811 B2 | 11/2010 |

OTHER PUBLICATIONS

English Abstract only of JP 2006-191989 dated Jul. 27, 2006.
International Search Report dated Jul. 17, 2012 issued in PCT/JP2012/064085.

*Primary Examiner* — Shan Elahi
(74) *Attorney, Agent, or Firm* — Scully, Scott, Murphy & Presser, P.C.

(57) ABSTRACT

Provided is a fluorescence observation apparatus including a fluorescence-image generating portion that generates a plurality of fluorescence images by capturing fluorescence from an observation subject at a time interval; a position identifying portion that, in the individual fluorescence images generated by the fluorescence-image generating portion, identifies high-luminance positions having gradation values equal to or greater than a predetermined threshold; a storage portion that stores the high-luminance positions identified by the position identifying portion; a track-image generating portion that generates a track image that has gradation values at the plurality of high-luminance positions stored in (Continued)

the storage portion; and a display portion that displays the track image generated by the track-image generating portion.

14 Claims, 10 Drawing Sheets

(51) Int. Cl.
    *G06T 7/20*     (2006.01)
    *G01N 21/64*     (2006.01)
    *A61B 1/00*     (2006.01)
    *A61B 1/04*     (2006.01)

(52) U.S. Cl.
    CPC ......... *A61B 1/043* (2013.01); *G01N 21/6456* (2013.01); *G06T 7/0083* (2013.01); *G06T 7/0097* (2013.01); *G06T 7/2033* (2013.01); *G06T 2207/10064* (2013.01); *G06T 2207/10068* (2013.01); *G06T 2207/30004* (2013.01); *G06T 2207/30241* (2013.01)

(58) Field of Classification Search
    USPC .......................................... 348/68
    See application file for complete search history.

(56) References Cited

U.S. PATENT DOCUMENTS

| | | | | |
|---|---|---|---|---|
| 2002/0168158 A1* | 11/2002 | Furusawa | ............. | A61B 1/042 385/116 |
| 2005/0099824 A1* | 5/2005 | Dowling | ............. | A61B 1/0653 362/572 |
| 2006/0173358 A1* | 8/2006 | Xie | .................... | A61B 1/00009 600/476 |
| 2006/0247535 A1* | 11/2006 | Sendai | ............... | A61B 1/00009 600/476 |
| 2007/0223797 A1* | 9/2007 | Kaneko | ............. | A61B 1/00009 382/128 |
| 2008/0055718 A1* | 3/2008 | Kono | ................. | G01N 21/6458 359/381 |
| 2009/0270678 A1* | 10/2009 | Scott | ................. | A61B 1/00009 600/109 |
| 2009/0274360 A1* | 11/2009 | Suzuki | ............... | G01N 21/6428 382/133 |
| 2010/0198010 A1* | 8/2010 | Cline | ................. | A61B 1/00009 600/109 |
| 2010/0204544 A1* | 8/2010 | Takei | ..................... | A61B 1/041 600/109 |
| 2010/0210904 A1* | 8/2010 | Cline | ................. | A61B 1/00009 600/109 |
| 2011/0012025 A1* | 1/2011 | Takei | ..................... | A61B 1/043 250/458.1 |
| 2011/0017923 A1* | 1/2011 | Kubo | ................. | A61B 1/00009 250/458.1 |
| 2011/0064296 A1* | 3/2011 | Dixon | ............... | G01N 21/6428 382/133 |
| 2011/0249137 A1* | 10/2011 | Suzuki | ............... | G01N 21/6428 348/222.1 |
| 2012/0184812 A1* | 7/2012 | Terakawa | ........... | A61B 1/00009 600/109 |
| 2012/0184813 A1* | 7/2012 | Terakawa | ........... | A61B 1/00009 600/109 |
| 2013/0235258 A1* | 9/2013 | Shida | ................. | A61B 1/00009 348/370 |
| 2014/0028824 A1* | 1/2014 | Kubo | ................... | A61B 5/0071 348/77 |
| 2014/0037179 A1* | 2/2014 | Shida | .................. | A61B 5/0033 382/132 |
| 2014/0128680 A1* | 5/2014 | Shida | .................... | A61B 1/043 600/178 |
| 2014/0184769 A1* | 7/2014 | Ishihara | ............. | A61B 1/00009 348/68 |
| 2014/0301617 A1* | 10/2014 | Shida | ................. | A61B 1/00009 382/128 |
| 2015/0257635 A1* | 9/2015 | Kubo | .................... | G02B 23/26 600/109 |

* cited by examiner

FLUORESCENCE OBSERVATION APPARATUS AND FLUORESCENCE OBSERVATION METHOD

CROSS-REFERENCE TO RELATED APPLICATIONS

This is a continuation of International Application PCT/JP2012/064085, with an international filing date of May 31, 2012, which is hereby incorporated by reference herein in its entirety. This application claims the benefit of Japanese Patent Application No. 2011-125524, the content of which is incorporated herein by reference.

TECHNICAL FIELD

The present invention relates to a fluorescence observation apparatus and a fluorescence observation method.

BACKGROUND ART

In the related art, there is a known fluorescence endoscope apparatus that acquires a fluorescence image and that has a means for reporting the detection of a region having a greater gradation value than a predetermined threshold in the fluorescence image (for example, see Patent Literature 1).

CITATION LIST

Patent Literature

{PTL 1} Publication of Japanese Patent No. 4587811

SUMMARY OF INVENTION

A first aspect of the present invention is a fluorescence observation apparatus including a fluorescence-image generating portion that generates a plurality of fluorescence images by capturing fluorescence generated at an observation subject at a time interval; a position identifying portion that, in the individual fluorescence images generated by the fluorescence-image generating portion, identifies high-luminance positions having gradation values equal to or greater than a predetermined threshold; a storage portion that stores the high-luminance positions identified by the position identifying portion; a track-image generating portion that generates a track image that has gradation values at the plurality of high-luminance positions stored in the storage portion; and a display portion that displays the track image generated by the track-image generating portion.

A second aspect of the present invention is a fluorescence observation apparatus including a fluorescence-image generating portion that generates a plurality of fluorescence images by capturing fluorescence generated at an observation subject at a time interval; a position identifying portion that, at the individual positions in the fluorescence images generated by the fluorescence-image generating portion, identifies high-luminance-change positions at which maximum gradation values thereof are equal to or greater than a first threshold and at which gradation values thereof exhibit degrees of change equal to or greater than a second threshold; a storage portion that stores the high-luminance-change positions identified by the position identifying portion; a display portion that displays the track image generated by the track-image generating portion.

A third aspect of the present invention is a fluorescence observation method including generating a plurality of fluorescence images by capturing fluorescence generated at an observation subject at a time interval; identifying high-luminance positions having gradation values equal to or greater than a predetermined threshold in the generated individual fluorescence images; storing the identified high-luminance positions; generating a track image that has gradation values at the plurality of stored high-luminance positions; and displaying the generated track image.

A fourth aspect of the present invention is a fluorescence observation method including generating a plurality of fluorescence images by capturing fluorescence generated at an observation subject at a time interval; identifying, at the individual positions in the generated fluorescence images, high-luminance-change positions at which maximum gradation values thereof are equal to or greater than a first threshold and at which gradation values thereof exhibit degrees of change equal to or greater than a second threshold; storing the identified high-luminance positions; generating a track image that has gradation values at the plurality of stored high-luminance-change positions; and displaying the generated track image.

DESCRIPTION OF EMBODIMENT

A fluorescence observation apparatus and a fluorescence observation method according to an embodiment of the present invention will be described below with reference to the drawings.

Figure 1:
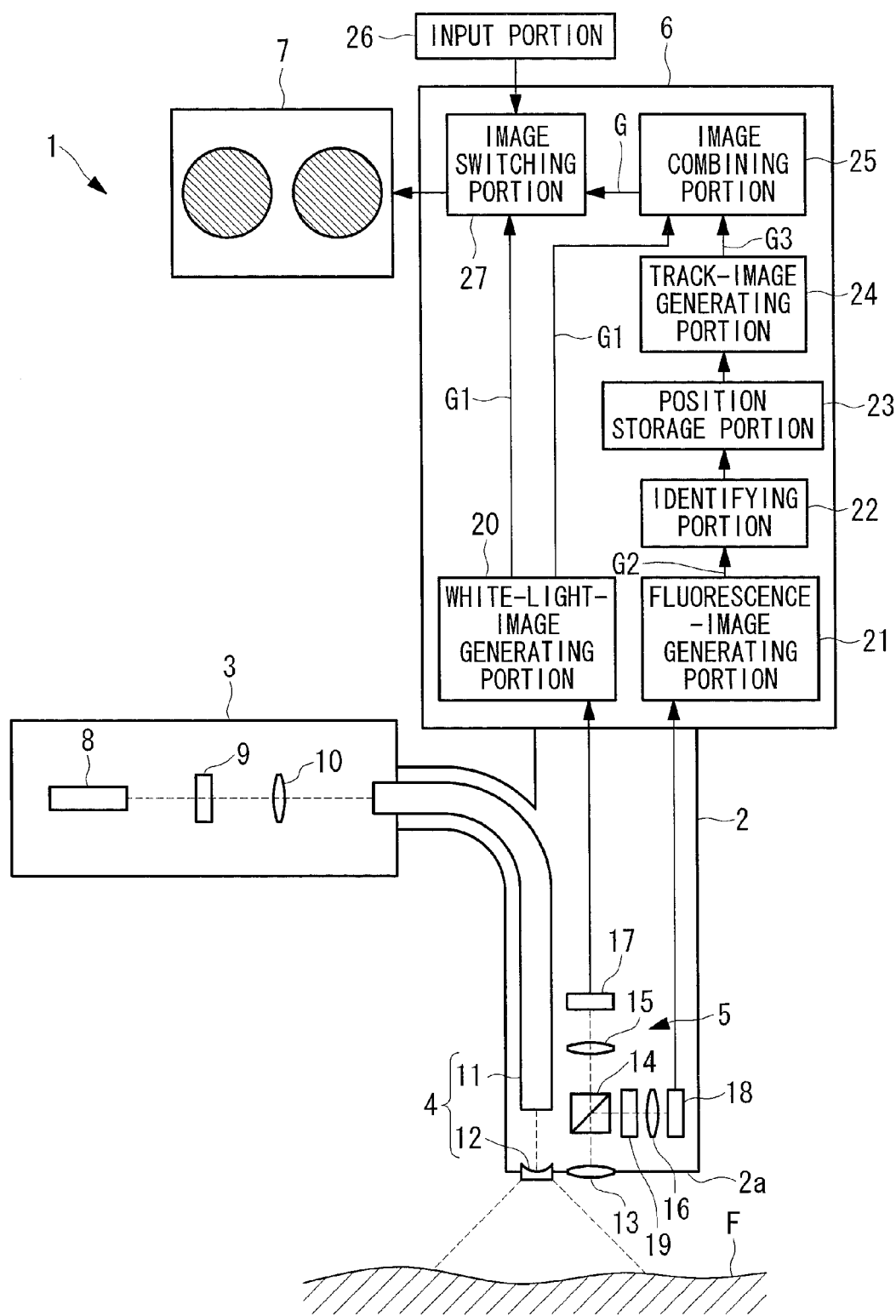
FIG. 1 is a diagram showing the overall configuration of a fluorescence observation apparatus according to an embodiment of the present invention.

A fluorescence observation apparatus 1 according to this embodiment is an endoscope apparatus provided with, as shown in FIG. 1, a long, thin inserted portion 2 that is inserted into a body; a light source 3; an illuminating unit 4 that radiates excitation light and illumination light from the light source 3 toward an observation subject F from the distal end of the inserted portion 2; an image-acquisition unit 5 that is provided at the distal end of the inserted portion 2 and that acquires image information about biological tissue, that is, the observation subject F; an image processing portion 6 that is disposed at the base side of the inserted portion 2 and that processes the image information acquired by the image-acquisition unit 5; and a monitor 7 that displays an image G that is processed by the image processing portion 6.

The light source 3 is provided with a xenon lamp 8; a filter 9 that extracts the excitation light and the white light (illumination light in a wavelength band of 400 nm to 740 nm) from the light emitted from the xenon lamp 8; and a coupling lens 10 that focuses the excitation light and the white light extracted by the filter 9.

The illuminating unit 4 is provided with a light-guide fiber 11 that is disposed along nearly the entire length of the inserted portion 2 in the longitudinal direction thereof and that guides the excitation light and the white light focused by the coupling lens 10; and an illumination optical system 12 that is provided at the distal end of the inserted portion 2, that spreads out the excitation light and the white light guided thereto by the light-guide fiber 11, and that radiates them onto the observation subject F facing a distal-end surface 2a of the inserted portion 2.

The image-acquisition unit 5 is provided with an objective lens 13 that collects light returning from a predetermined observation area of the observation subject F; a dichroic mirror 14 that, of the light collected by the objective lens 13, reflects light having an excitation wavelength or greater (excitation light and fluorescence) and allows white light (return light) having a wavelength less than the excitation wavelength to pass therethrough; two focusing lenses 15 and 16 that respectively focus the fluorescence reflected by the dichroic mirror 14 and the white light that has passed through the dichroic mirror 14; and two image-acquisition devices 17 and 18, such as CCDs, that capture the white light and the fluorescence focused by the focusing lenses 15 and 16. In the figures, reference sign 19 indicates an excitation-light cut filter that blocks the excitation light in the light reflected by the dichroic mirror (allows only the light in a wavelength band of, for example, 760 nm to 850 nm to pass therethrough).

The image processing portion 6 is provided with a white-light-image generating portion 20 that generates a white-light image G1 based on white-light-image information acquired by the image-acquisition device 17; a fluorescence-image generating portion 21 that generates a fluorescence image G2 based on fluorescence-image information acquired by the image-acquisition device 18; an identifying portion (position identifying portion) 22 that, in the fluorescence image G2 generated by the fluorescence-image generating portion 21, identifies pixels having gradation values equal to or greater than a threshold set in advance (high-luminance pixels) and that outputs the pixel positions (coordinates) thereof; a position storage portion 23 that stores the pixel positions identified by the identifying portion 22; a track-image generating portion 24 that generates a track image G3 that has gradation values at all positions stored in the position storage portion 23; and an image combining portion 25 that generates a superimposed image G by superimposing the white-light image G1 and the track image G3.

In the figures, reference sign 26 indicates an input portion for an examiner to input an image switching instruction. Reference sign 27 indicates an image switching portion that switches the image to be sent to the monitor 7 between the white-light image G1 and the superimposed image G in accordance with the image switching instruction input via the input portion 26.

The image-acquisition devices 17 and 18 acquire white-light-image information and fluorescence-image information at a certain frame rate.

The identifying portion 22 compares gradation values of individual pixels of the fluorescence image G2, which is transmitted thereto from the fluorescence-image generating portion 21, with the predetermined threshold; identifies pixels having gradation values that are equal to or greater than the threshold; and outputs the positions thereof to the position storage portion 23.

At the point in time when the first pixel position is received from the identifying portion 22 after starting observation, the position storage portion 23 starts to store that position. Thereafter, the position storage portion 23 continues to store pixel positions for a set number (for example, 25) of fluorescence images G2. Then, at the point in time when pixel position storage is completed for the set number of fluorescence images G2, the position storage portion 23 outputs all stored pixel positions to the track-image generating portion 24.

The track-image generating portion 24 generates a track image G3 in which a certain gradation value is assigned to all pixel positions transmitted thereto from the position storage portion 23. In other words, even if a high-luminance region moves in the fluorescence images G2 due to the movement of a fluorescent substance in the observation subject F, a track image G3 is generated reflecting the track of this movement. Therefore, it is possible to determine the shape of an organ through which the fluorescent substance has moved by using the track image G3.

The operation of the thus-configured fluorescence observation apparatus 1 according to this embodiment will be described below.

To observe biological tissue in the body, which is the observation subject F, by using the fluorescence observation apparatus 1 according to this embodiment, the inserted portion 2 is inserted into the body and the distal-end surface 2a of the inserted portion 2 is disposed so as to face the observation subject F. Then, the light source 3 is activated to generate the excitation light and the white light, which are made to enter the light-guide fiber 11 by the coupling lens 10. The excitation light and the white light that have reached the distal end of the inserted portion 2 by being guided thereto by the light-guide fiber 11 are spread out and radiated onto the observation subject F by the illumination optical system 12 provided at the distal end of the inserted portion 2.

At the observation subject F, a fluorescent substance contained therein is excited by the excitation light, causing fluorescence to be emitted, and the white light is reflected at the surface of the observation subject F. The fluorescence and the reflected white light return to the distal-end surface 2a of the inserted portion 2 from the observation subject F, and the fluorescence and white light emitted from a portion of the observation subject F, that is, an observation area, are collected by the objective lens 13.

Figure 2:
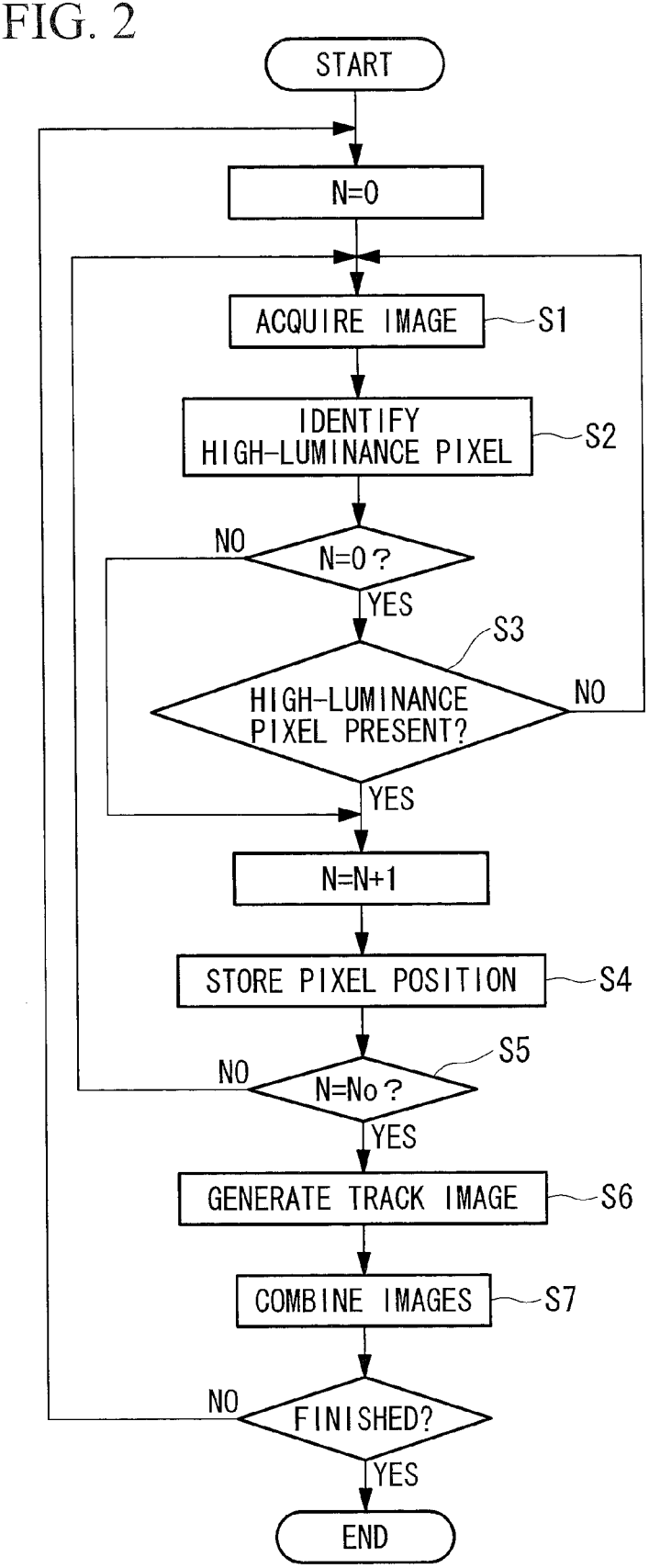
FIG. 2 is a flowchart for explaining the superimposed-image generating processing performed in the fluorescence observation apparatus in FIG. 1.

FIG. 2 shows a flowchart for explaining the fluorescence observation method according to this embodiment, that is, processing for generating a superimposed image, performed in the fluorescence observation apparatus 1.

The fluorescence and the white light collected by the objective lens 13 are split by the dichroic mirror 14 in accordance with the wavelength thereof, and, for example, the white light in a wavelength band of 400 nm to 700 nm is focused by the focusing lens 15 and acquired by the image-acquisition device 17 as the white-light-image information (Step S1).

Of the fluorescence and the white light collected by the objective lens 13, excitation light (for example, light having a wavelength equal to or less than 740 nm) is removed by the excitation-light cut filter 19 from light reflected at the dichroic mirror 14, for example, light containing the excitation light and the fluorescence in a wavelength band of 700 nm to 850 nm, and thus, only the fluorescence is subsequently focused by the focusing lens 16 and is acquired by the image-acquisition device 18 as the fluorescence-image information (fluorescence image generating step S1).

The image information acquired by the respective image-acquisition devices 17 and 18 is transmitted to the image processing portion 6. At the image processing portion 6, the white-light-image information is input to the white-light-image generating portion 20, where a white-light image G1 is generated. On the other hand, the fluorescence-image information is input to the fluorescence-image generating portion 21, where a fluorescence image G2 is generated.

Figure 3A:
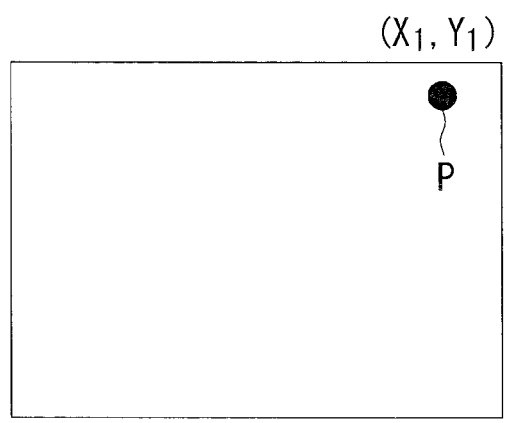
FIG. 3A is a diagram for explaining the track-image generating processing performed in the fluorescence observation apparatus in FIG. 1 and is a diagram showing an example image in which a first high-luminance pixel is shown.
Figure 3B:
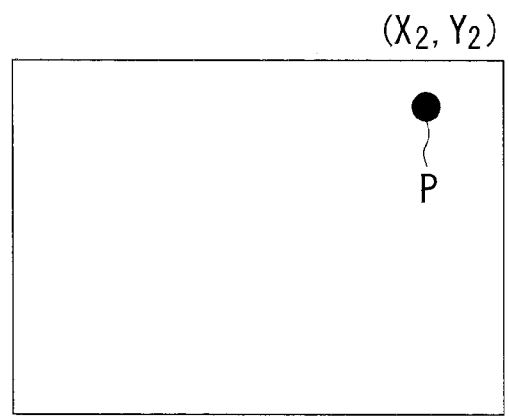
FIG. 3B is a diagram for explaining the track-image generating processing performed in the fluorescence observation apparatus in FIG. 1, and is a diagram showing an example image in which a second high-luminance pixel is shown.

The generated fluorescence image G2 is transmitted to the identifying portion 22, where, as shown in FIGS. 3A and 3B, pixels (high-luminance pixels) P having gradation values equal to or greater than the predetermined threshold are identified (position identifying step S2). If high-luminance pixels P do not exist, the process returns to Step S1 and a next image is acquired (Step S3). If the high-luminance pixels P exist, the positions (coordinates) of the identified high-luminance pixels P are output to the position storage portion 23 from the identifying portion 22 and are stored in the position storage portion 23 (storing step S4).

Figure 3C:
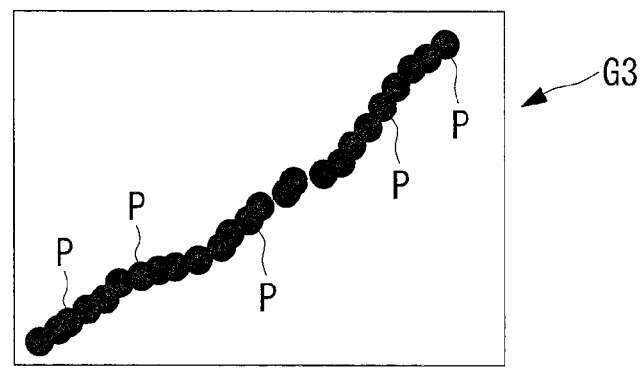
FIG. 3C is a diagram for explaining the track-image generating processing performed in the fluorescence observation apparatus in FIG. 1 and is a diagram showing an example image of a track image.

Then, it is judged whether or not the positions of the high-luminance pixels P have been stored for the predetermined number (here, $N_0$=25) of the fluorescence images G2 (Step S5), and, at the point in time when the positions have been stored for the predetermined number $N_0$ of images, all stored positions of the high-luminance pixels P are output to the track-image generating portion 24 from the position storage portion 23. At the track-image generating portion 24, as shown in FIG. 3C, a track image G3 having a certain gradation value only at all positions of the high-luminance pixels P transmitted thereto from the position storage portion 23 is generated (track-image generating step S6).

At the image combining portion 25, the generated track image G3 is superimposed on the white-light image G1 transmitted thereto from the white-light-image generating portion 20 (Step S7). The generated superimposed image G is output from the image combining portion 25 (displaying step). On the basis of the superimposed image G in which the track image G3 representing the track of the high-luminance pixels P is superposed on the white-light image G1 representing the morphological feature of the observation subject F, an examiner can observe the track image G3 in association directly with the observation subject F.

By inputting a switching instruction via the input portion 26, the examiner can operate the image switching portion 27 so as to display the white-light image G1 or the superimposed image G on the monitor 7 by switching between them.

As described above, with the fluorescence observation apparatus 1 according to this embodiment, when the examiner inputs the switching instruction via the input portion 26, the track image G3, which has gradation values at positions of the high-luminance pixels P that have gradation values equal to or greater than the threshold and that have been identified in the predetermined number of fluorescence images G2 acquired at certain time intervals, is displayed by being superimposed on the white-light image G1. Even in the case in which a fluorescent substance moves in the observation subject F, the movement track thereof can be determined based on this superimposed image G.

For example, as in the case of fluorescence from a liquid flowing in urethra, which contains a fluorescent substance, high-intensity fluorescence moving in the observation subject F will be located at different positions in a plurality of fluorescence images G2 generated at certain time intervals. With the track image G3 that has gradation values at all of these high-luminance pixels P, the movement track of the fluorescence, that is, the shape of an organ such as urethra or the like, can be satisfactorily represented. As a result, there is an advantage in that, even with an organ such as the ureter or the like in which fluorescence cannot constantly be generated, the shape thereof can be determined in a simple manner.

In this embodiment, the following modifications may be employed.

First, in this embodiment, although the number of fluorescence images G2 to be acquired to identify the high-luminance pixels P is fixed to the predetermined set number $N_0$ of images (for example, 25), alternatively, the number may be changed as described below.

Figure 4:
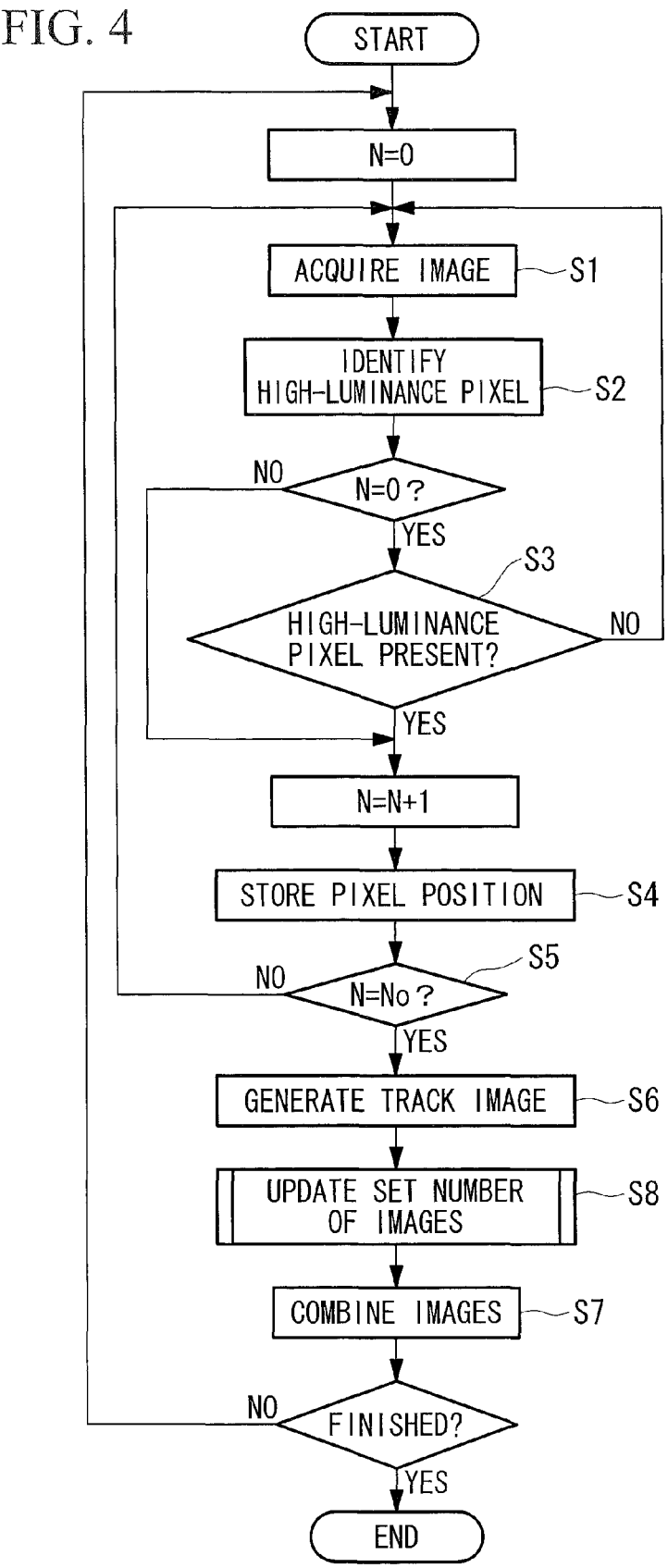
FIG. 4 is a flowchart for explaining superimposed-image generating processing performed in a first modification of the fluorescence observation apparatus in FIG. 1.

Specifically, at the point in time at which a track image G3 is generated based on the first group of fluorescence images G2 in the set number $N_0$ of images, the process advances to a set-number-of-images updating step S8, as shown in FIG. 4.

Figure 5:
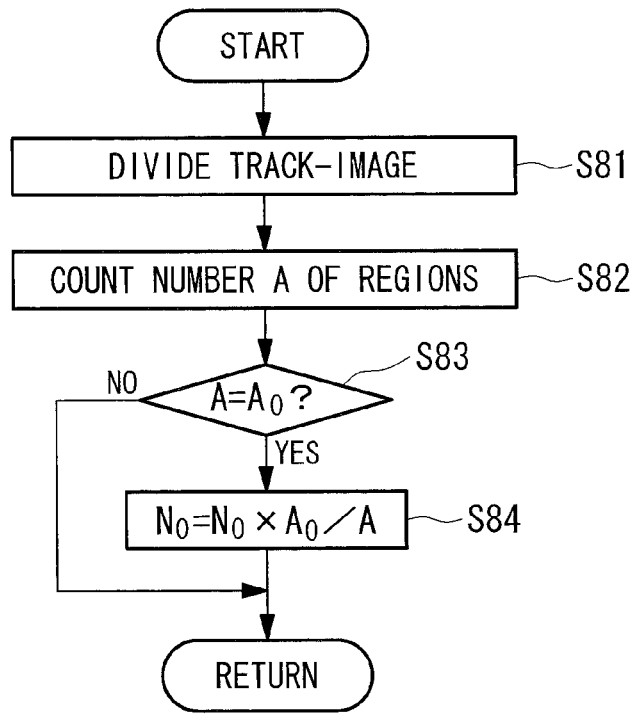
FIG. 5 is a flowchart for explaining the set-number-of-images updating processing performed in the fluorescence observation apparatus in FIG. 4.
Figure 6:
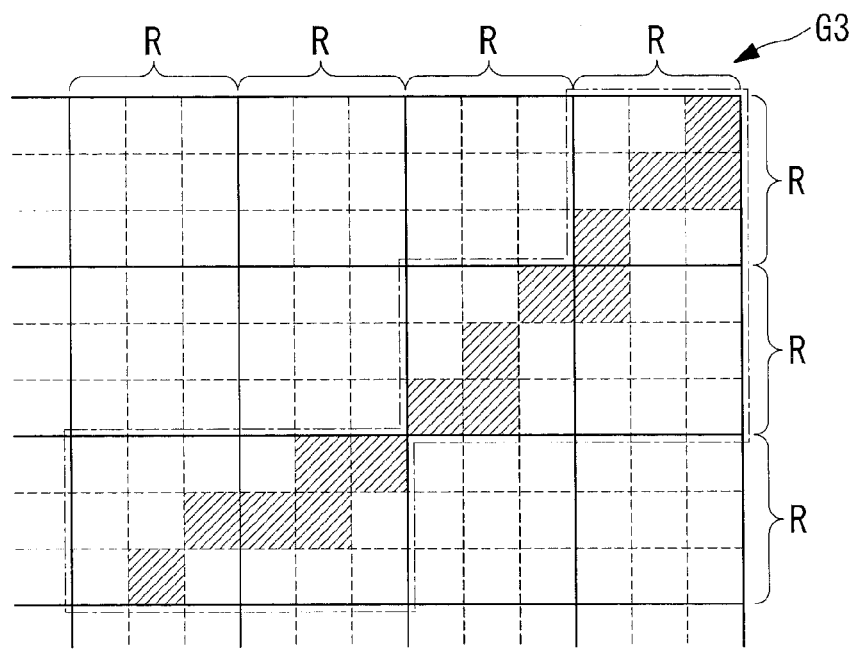
FIG. 6 is a diagram for explaining region division and counting of the number of regions performed in the fluorescence observation apparatus in FIG. 4.

As shown in FIGS. 5 and 6, in the set-number-of-images updating step S8, the entire generated track image G3 is divided into a plurality of regions R formed of a plurality of pixels (3×3=9 pixels in the example shown in FIG. 6) (Step S81), and the number A of regions R (regions surrounded by the chain line) that have at least one pixel having the gradation value equal to or greater than the threshold (indicated by hatching) is counted (Step S82). In FIG. 6, the number A of these regions is 5. Then, it is judged whether or not the counted number A of the regions is equal to or less than a predetermined number-of-regions threshold $A_0$ (Step S83), and the set number $N_0$ of images should be increased when the counted number of regions is equal to or less than the predetermined number-of-regions threshold $A_0$.

For example, in FIG. 5, it is assumed that the initial set number $N_0$ is 10 and the number-of-regions threshold $A_0$ at which it can be judged that a track of a sufficient length is displayed in a track image G3 as a whole is 50. In the case in which the counted number A of the regions is 20, the set number $N_0$ of the fluorescence images G2 to be acquired to generate a track image G3 should be updated to 25, that is, 2.5 (=50÷20) times the initial value (Step S84).

In a case where the speed at which a fluorescent substance moves in the observation subject F is slow, the track represented in the track image G3 may be extremely short when the initially set set number $N_0$ of images is used. Therefore, by updating the set number $N_0$ of images as described above, there is an advantage in that it is possible to generate a track image G3 in which a sufficiently long track is represented.

Second, the size of the divided regions depends on the observation conditions. Specifically, with observation conditions in which the fluorescent substance in the observation subject F is observed at a relatively large size, the size of the individual divided regions is increased by decreasing the number of divisions. On the other hand, with observation conditions in which the fluorescent substance is observed at a relatively small size, it is preferable to decrease the size of the individual divided regions by increasing the number of divisions.

Figure 7:
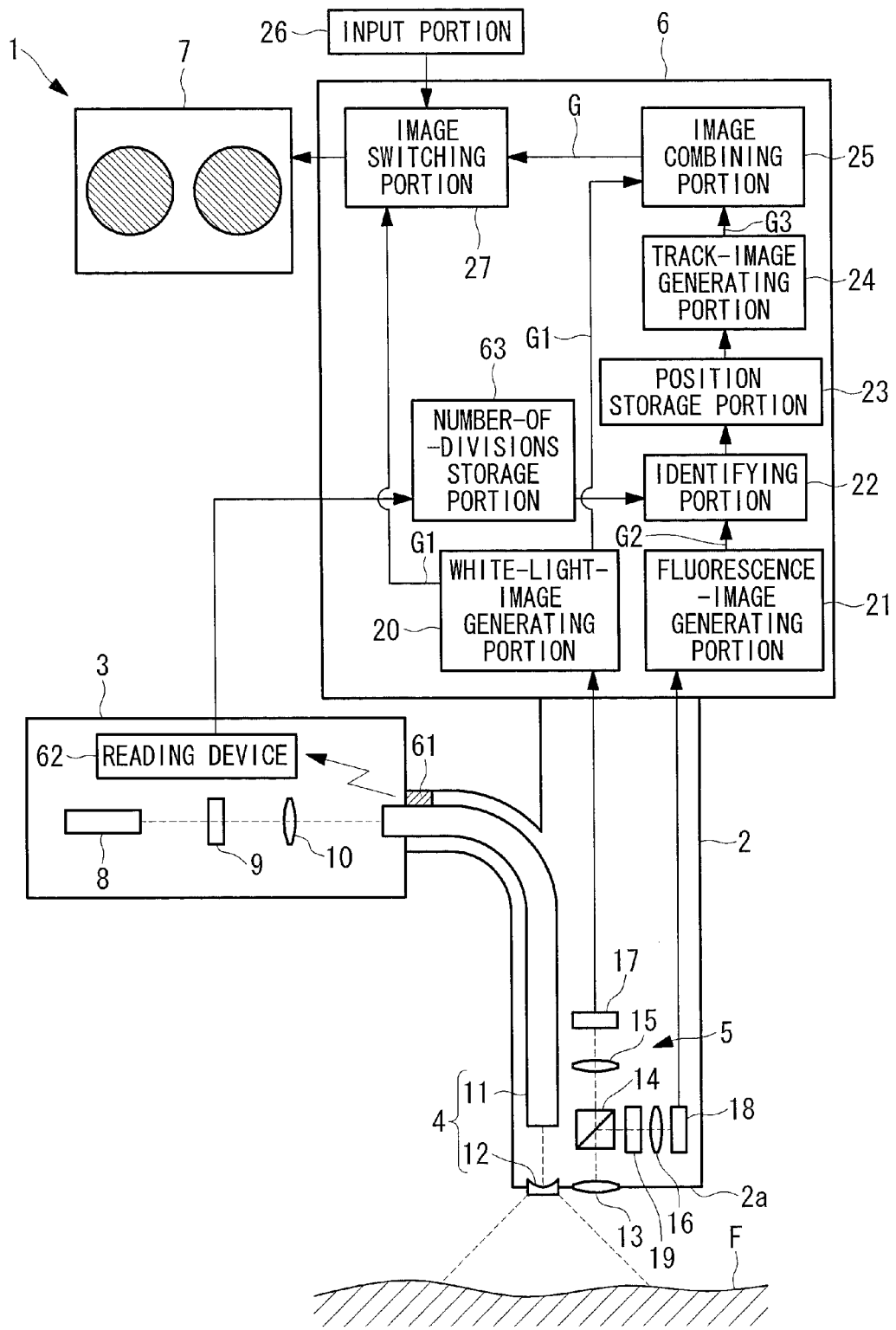
FIG. 7 is a diagram showing the overall configuration of a second modification of the fluorescence observation apparatus in FIG. 1.

For this purpose, as shown in FIG. 7, the fluorescence observation apparatus 1 may be provided with an inserted portion (attachable/detachable component) 2 that can be attached to and detached from the light source 3 and the image processing portion 6, so that the inserted portion 2 can be exchanged in accordance with a site serving as the observation subject, and the inserted portion 2 may be provided with an IC chip 61 that stores identification information of the inserted portion 2. The light source 3 to which the inserted portion 2 is attached is provided with a reading device 62 that reads the identification information in the IC chip 61.

Furthermore, the image processing portion 6 is provided with a number-of-divisions storage portion 63 that stores the identification information and the number of divisions in association with each other. The number-of-divisions storage portion 63 is connected to the identifying portion 22.

When an inserted portion 2 is attached, the identification information in the IC chip 61 provided in that inserted portion 2 is read by the reading device 62 and is transmitted to the image processing portion 6.

At the image processing portion 6, a number of divisions corresponding to the identification information transmitted thereto is read out from the number-of-divisions storage portion 63, and thus, it is easily determined whether or not the number of regions R of interest identified by the identifying portion 22 is a sufficiently high number to generate a track image.

Accordingly, it is possible to set an appropriate number of divisions, that is, the size of the individual divided regions, in accordance with the observation conditions in a simple manner.

Figure 8:
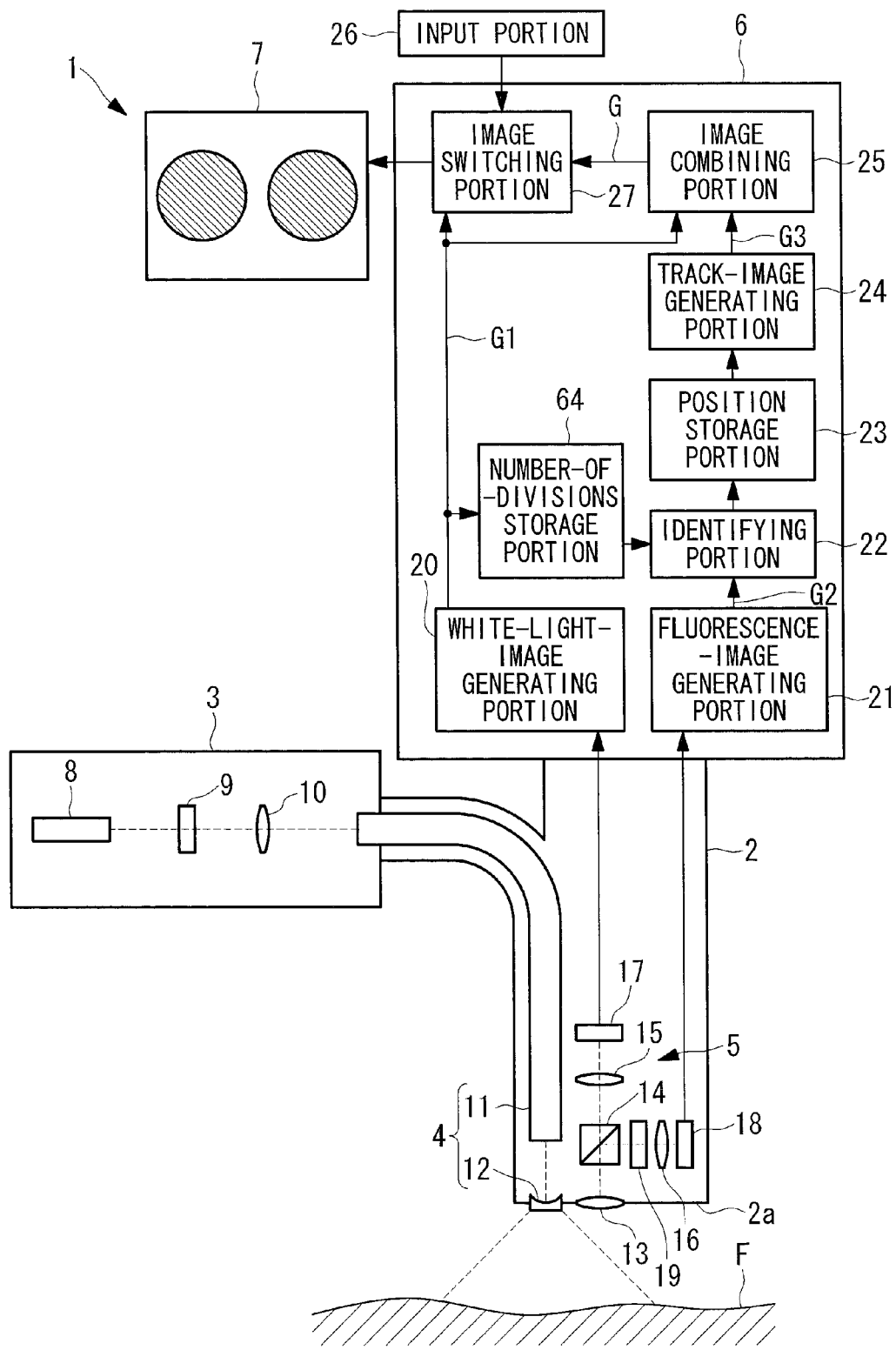
FIG. 8 is a diagram showing the overall configuration of a third modification of the fluorescence observation apparatus in FIG. 1.

Third, as shown in FIG. 8, instead of changing the number of divisions by means of attaching and detaching the inserted portion 2, luminance information of white-light images and the number of divisions may be stored in a number-of-divisions storage portion 64 in association with each other, and a number of divisions corresponding to luminance information, for example, an average luminance value, of a white-light image G1 generated by the white-light-image generating portion 20 may be read out from the number-of-divisions storage portion 64 and set in the identifying portion 22.

For example, by dividing a track image G3 by a lower number of divisions when the white-light image G1 is brighter and by dividing a track image G3 by a greater number of divisions when the white-light image G1 is darker, an appropriate track image G3 can be generated. Specifically, because the luminance of the white-light image G1 depends on the distance between the position irradiated with the illumination light and the observation subject F, when the luminance is high, the high-luminance regions to be observed appear large in the fluorescence images G2. Therefore, in such a case, by decreasing the number of divisions, that is, by increasing the size of the divided regions, an appropriate track image G3 can be generated.

Figure 9:
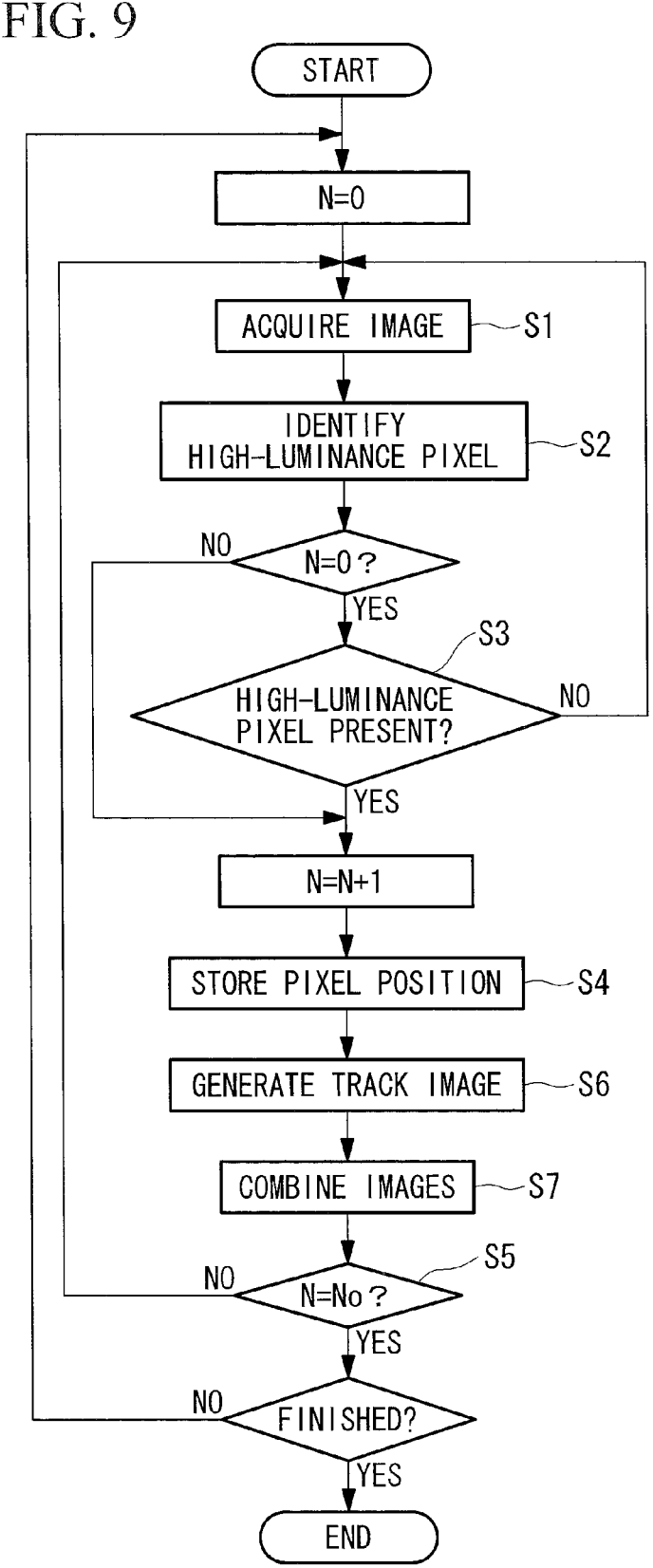
FIG. 9 is a flowchart for explaining the superimposed-image generating processing performed in a fourth modification of the fluorescence observation apparatus in FIG. 1.

Fourth, in this embodiment, although the track image G3 is generated after identifying the high-luminance pixels P in the set number $N_0$ of the fluorescence images G2, alternatively, the track image G3 may be updated each time one fluorescence image G2 is acquired, as shown in FIG. 9.

By doing so, it is possible to display a movement track in the superimposed image G on the monitor 7 so that the movement track grows with the movement of the fluorescent substance. Accordingly, there is an advantage in that it is possible to observe the shape of an organ with even greater real-time performance. In this case, at the point in time when processing of the set number $N_0$ of images is completed, a previously generated track image G3 is deleted and generation of a new track image G3 begins; thus, observation can be performed by using the most recent track image G3.

Fifth, in this embodiment, although the track image G3 is generated by accumulating the positions of the high-luminance pixels P individually identified from the set number $N_0$ of fluorescence images G2, alternatively, maximum gradation values B and difference values C between those maximum gradation values and minimum gradation values may be determined for the individual pixels after acquiring the set number $N_0$ of fluorescence images G2, and pixels in which the maximum gradation values B are equal to or greater than a first threshold and in which the difference values C are also equal to or greater than a second threshold may be identified as the high-luminance pixels P.

Figure 10:
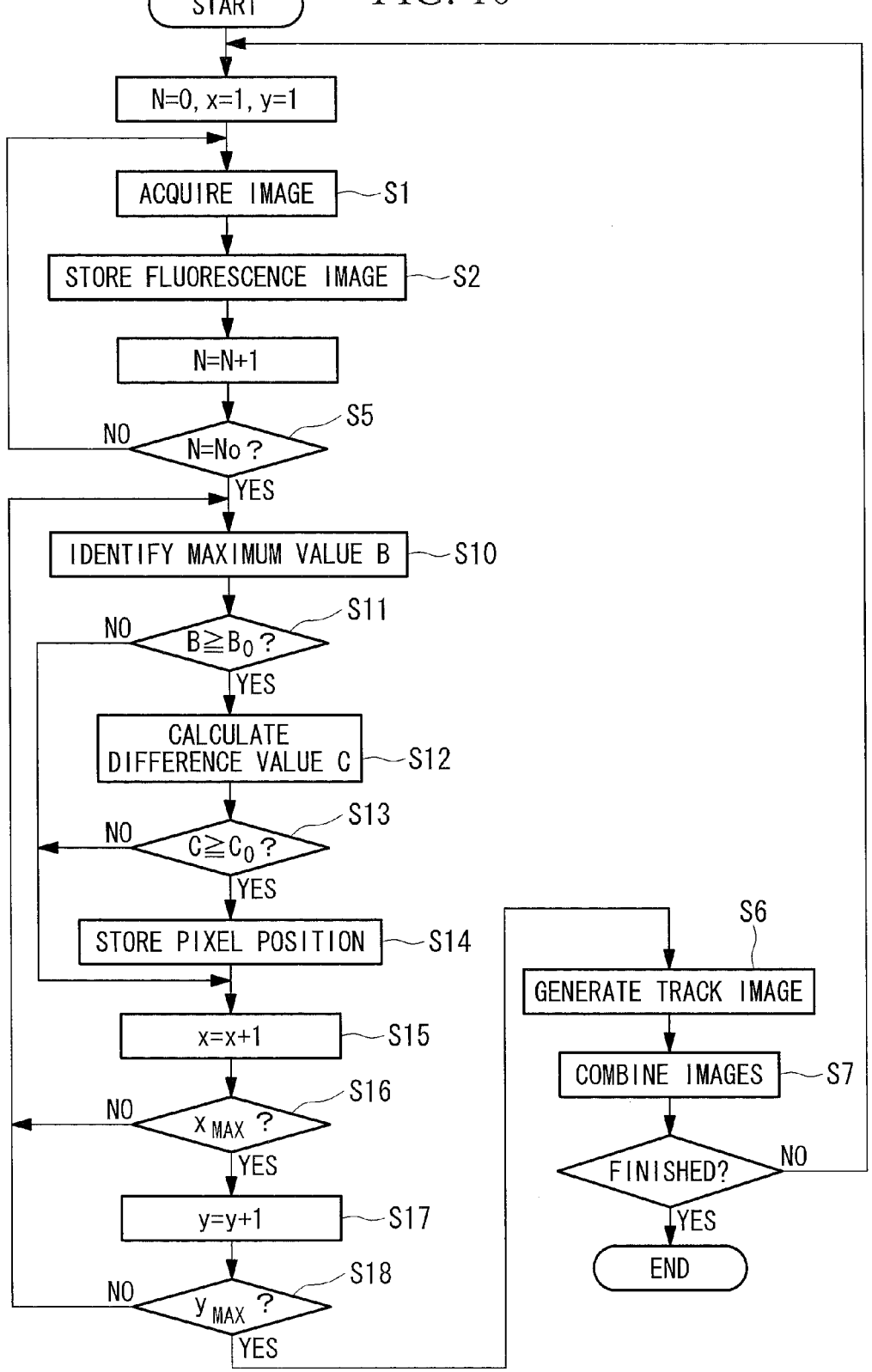
FIG. 10 is a flowchart for explaining the superimposed-image generating processing performed in a fifth modification of the fluorescence observation apparatus in FIG. 1.

Specifically, as shown in FIG. 10, the set number $N_0$ of fluorescence images G2 are stored, the maximum gradation values B are identified in the individual fluorescence images G2 (position identifying step S10), and it is judged whether or not the identified maximum gradation values B are equal to or greater than the first threshold $B_0$ (position identifying step S11). By doing so, desired high-luminance pixels P emitting more intense fluorescence are precisely identified. When the maximum gradation values B are equal to or greater than the first threshold $B_0$, the difference values C between the maximum gradation values B and the minimum gradation values are calculated (position identifying step S12), and it is judged whether or not the calculated difference values C are equal to or greater than the second threshold $C_0$ (position identifying step S13). These difference values C represent the degrees of change in the gradation values of the pixels having the maximum gradation values B among the plurality of fluorescence images G2, in other words, the degrees of change in the gradation values in the time-axis direction, and are equivalent to the degrees of change over time in the fluorescence intensity at the positions in the observation subject F corresponding to these pixels.

When the difference values C are equal to or greater than the second threshold, the pixel positions thereof are stored (storing step S14). By identifying the positions at which the gradation values change with the degree of change equal to or greater than the second threshold $C_0$ in this way, positions through which fluorescence has moved are identified in more detail.

Accordingly, positions are stored for the pixels at which the maximum gradation values B are equal to or greater than the first threshold $B_0$ and at which the difference values C are equal to or greater than the second threshold $C_0$.

When a maximum gradation value B is less than the first threshold $B_0$, or when a difference value C is less than the second threshold $C_0$, the pixel is shifted in the x-direction or the y-direction without storing the pixel position, and the same judgment is made on the next pixel. By repeating processing from Step S10 to Step S14 until reaching $x=x_{MAX}$ and $y=y_{MAX}$ (Step S15 to Step S18), the above-described judgment is made for all pixels.

Then, after the judgment is made for all pixels, the position storage portion 23 outputs all pixel positions at which the above-described conditions are met to the track-image generating portion 24. The track-image generating portion 24 generates a track image G3 that has gradation values only at these pixel positions (track-image generating step).

By doing so, there is an advantage in that it is possible to prevent the problem of non-moving high-luminance pixels P being identified as a track, thus making it possible to provide the examiner with a more accurate track of the fluorescent substance.

Note that, in this fifth modification, instead of the difference values C between the maximum gradation values B and the minimum gradation values, time derivative values of the gradation values may be employed as the degrees of change in the gradation values at individual positions in the fluorescence images G2. Specifically, for the pixels having the maximum gradation values B, gradation values are identified from a plurality of fluorescence images G2 arranged in the time-axis direction, time derivative values of the gradation values are determined based on the changes in the identified gradation values in the time-axis direction, and the calculated time derivative values are compared with the second threshold. Then, when the time derivative values are equal to or greater than the second threshold, those pixel positions are stored. In this way also, it is possible to selectively identify the positions at which the fluorescence intensity exhibits a sufficiently large degree of change over time.

Figure 11A:
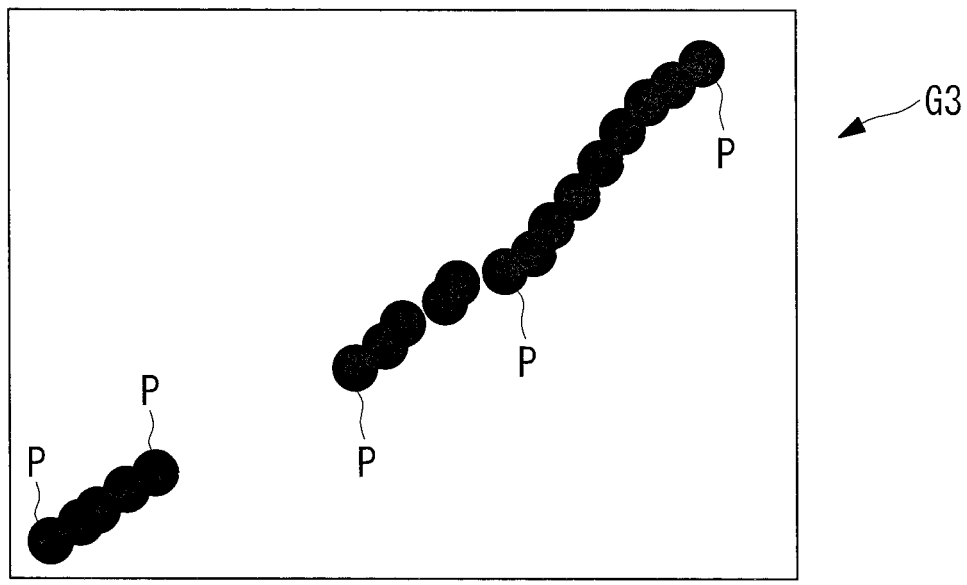
FIG. 11A is a diagram showing a track image, which is generated by a sixth modification of the fluorescence observation apparatus in FIG. 1 and which has a gap therein.
Figure 11B:
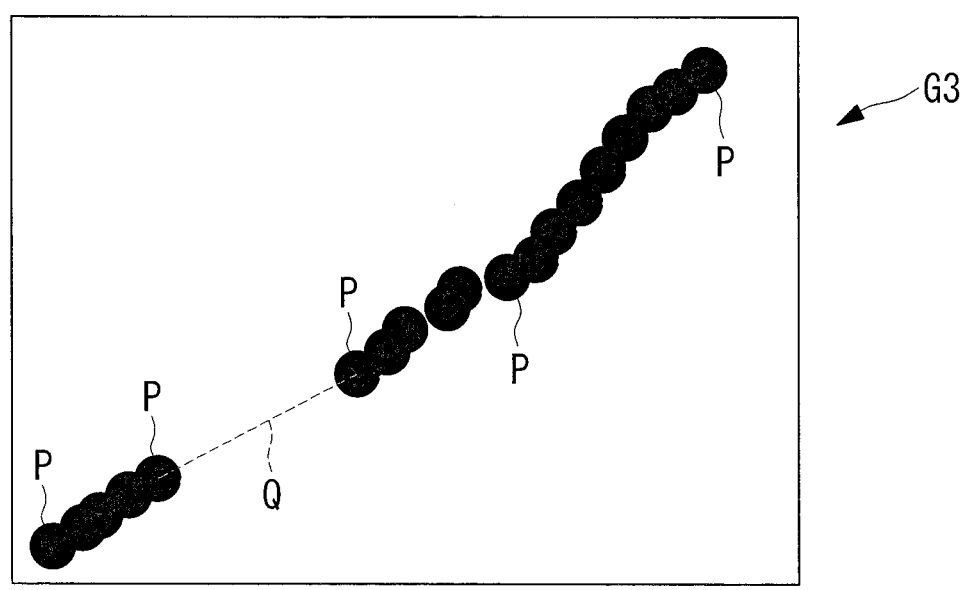
FIG. 11B is a diagram showing a track image, which is generated by the sixth modification of the fluorescence observation apparatus in FIG. 1 and which is interpolated by using a virtual track.

Sixth, when storing the positions of the high-luminance pixels P in the position storage portion 23, the positions may be stored in association with the times at which the high-luminance pixels P are identified. Then, when generating a track image G3 at the track-image generating portion 24 after identifying the high-luminance pixels P in the set number $N_0$ of fluorescence images G2, if there is a time at which high-luminance pixels P do not exist, a virtual track Q that connects the high-luminance pixels P at the positions immediately before and after that time may be generated, as shown in FIGS. 11A and 11B.

By doing so, when the time interval between times at which any two high-luminance pixels P stored in the storage portion 23 are identified is longer than the certain time interval at which the fluorescence images G2 are captured, it is clear that it is highly likely that the high-luminance pixels P are not identified at times falling within this period. For example, there may be a case in which, for reasons such as an organ such as the ureter or the like being partially hidden under adipose tissue or another organ, fluorescence from a fluorescent substance flowing in the interior thereof cannot be detected in some portions. Even in such a case, it is possible to estimate the position of a hidden organ such as the ureter or the like by connecting the detected high-luminance pixels P with each other by using the virtual track Q.

The virtual track Q may connect the high-luminance pixels P with each other in a straight line or may connect them in a curve estimated from the shapes of preceding and subsequent tracks. In addition, the virtual track Q may be generated by changing the color thereof from other portions of the track or as a chain line, so that the virtual track Q can be identified in the track image G3.

REFERENCE SIGNS LIST

A number of regions
B maximum gradation value
C difference value (difference)
F observation subject
G1 white-light image (return-light image)
G2 fluorescence image
G3 track image
P high-luminance pixel
R region
$N_0$ set number of images
$A_0$ number-of-regions threshold
1 fluorescence observation apparatus
2 inserted portion (attachable/detachable component)
7 monitor (display portion)
20 white-light-image generating portion (return-light-image generating portion)
21 fluorescence-image generating portion
22 identifying portion (position identifying portion, region dividing portion)
23 position storage portion (storage portion)
24 track-image generating portion
25 image combining portion
61 IC chip (identification-information storage portion)
62 reading device (identification information reading portion)

The invention claimed is:

1. A fluorescence observation apparatus comprising:
a processor comprising hardware, wherein the processor is configured to:
generate a plurality of fluorescence images based on fluorescence-image information, acquired at a predetermined time interval by an image sensor, of fluorescence generated at an observation subject;
identify high-luminance positions having gradation values equal to or greater than a predetermined threshold in the generated individual fluorescence images;
control a storage to store the high-luminance positions identified;
generate a track image that shows the plurality of high-luminance positions stored in the storage; and
control a display to display the track image.

2. The fluorescence observation apparatus according to claim 1,
wherein the processor is configured to:
control the image sensor to capture a set number of images of the observation subject;
generate the set number of fluorescence images;
divide the track image into a plurality of regions;
count the number of regions of the plurality of regions in which pixels having the gradation values equal to or greater than the predetermined threshold exist; and update the set number of images of the observation subject to be captured by the image sensor and the set number of fluorescence images to be generated in accordance with the number of regions counted.

3. The fluorescence observation apparatus according to claim 2,
wherein the processor is configured to update the set number so as to increase when the number of regions counted is less than a number-of-regions threshold.

4. The fluorescence observation apparatus according to claim 1, further comprising:
an attachable/detachable component configured to be attachable to and detachable from a light source for illuminating the observation subject and the processor, wherein the attachable/detachable component comprises:
the image sensor;
optical elements that determine observation conditions of the observation subject; and
an identification-information storage configured to store identification information of the optical elements; and
an identification-information reading device configured to read the identification information stored in the identification-information storage,
wherein the processor is configured to divide the fluorescence images into a plurality of regions in accordance with a number of divisions stored in association with the identification information read by the identification-information reading device.

5. The fluorescence observation apparatus according to claim 1,
wherein the processor is configured to:
generate a return-light image based on white-light-image information of captured return light returning from the observation subject when the observation subject is irradiated with illumination light; and
divide the fluorescence images into a plurality of regions in accordance with the number of divisions stored in association with luminance information of the generated return-light image.

6. The fluorescence observation apparatus according to claim 1,
wherein the processor is configured to:
identify the high-luminance positions each time the fluorescence images are generated; and
generate the track image each time the high-luminance positions are identified.

7. The fluorescence observation apparatus according to claim 6,
wherein the processor is configured to:
detect a time at which the generation of a track image corresponding to an observation area in the observation subject starts or a time at which the generation thereof ends; and
delete a previously generated track image at the point in time when the start of the generation of the track image or the end thereof is detected.

8. The fluorescence observation apparatus according to claim 1,
wherein the processor is configured to:
control the storage to store the high-luminance positions in association with times at which the high-luminance positions are identified; and
in response to determining that a time interval between times at which any two consecutively acquired high-luminance positions are identified is longer than the predetermined time interval, generate a virtual track between these two consecutively acquired high-luminance positions.

9. The fluorescence observation apparatus according to claim 1,
wherein the processor is configured to:
generate a return-light image based on white-light-image information of captured return light returning from the observation subject when the observation subject is irradiated with illumination light; and
generate a superimposed image in which the track image is superimposed on the return-light image; and
control the display to display the superimposed image.

10. A fluorescence observation apparatus comprising:
a processor comprising hardware, wherein the processor is configured to:
generate a plurality of fluorescence images based on fluorescence-image information, acquired at a predetermined time interval by an image sensor, of fluorescence generated at an observation subject;
identify high-luminance-change positions at which maximum gradation values thereof are equal to or greater than a first threshold and at which gradation values thereof exhibit degrees of change equal to or greater than a second threshold at the individual positions in the generated fluorescence images;
control a storage to store the high-luminance-change positions identified;
generate a track image that shows the plurality of high-luminance-change positions stored in the storage; and
control a display to display the track image.

11. The fluorescence observation apparatus according to claim 10,
wherein the processor is configured to:
identify maximum gradation values and minimum gradation values at the same positions in the plurality of generated fluorescence images; and
calculate the degree of change in the gradation values based on differences therebetween.

12. The fluorescence observation apparatus according to claim 10,
wherein the processor is configured to:
calculate time derivative values of the gradation values at the same positions in the plurality of generated fluorescence images; and
calculate the degree of change in the gradation values based on the calculated time derivative values.

13. A fluorescence observation method comprising:
generating a plurality of fluorescence images based on fluorescence-image information, acquired at a predetermined time interval by an image sensor, of fluorescence generated at an observation subject;
identifying high-luminance positions having gradation values equal to or greater than a predetermined threshold in the generated individual fluorescence images;
storing the identified high-luminance positions;
generating a track image that shows the plurality of stored high-luminance positions; and
displaying the generated track image.

14. A fluorescence observation method comprising:
generating a plurality of fluorescence images based on fluorescence-image information, acquired at a predetermined time interval by an image sensor, of fluorescence generated at an observation subject;
identifying high-luminance-change positions at which maximum gradation values thereof are equal to or greater than a first threshold and at which gradation values thereof exhibit degrees of change equal to or greater than a second threshold at the individual positions in the generated fluorescence images;
storing the identified high-luminance-change positions;
generating a track image that shows the plurality of stored high-luminance-change positions; and
displaying the generated track image.

* * * * *